United States Patent [19]

Isobe et al.

[11] 4,166,110
[45] Aug. 28, 1979

[54] NAIL ENAMEL COMPOSITION AND MANUFACTURING METHOD THEREOF

[75] Inventors: Kenichi Isobe, Annaka; Tatsuhiko Tsutsui, Tokyo; Takao Ueki, Fujisawa; Toru Sema, Yokohama, all of Japan

[73] Assignee: The Lion Dentrifice Co., Ltd., Tokyo, Japan

[21] Appl. No.: 873,850

[22] Filed: Jan. 31, 1978

[30] Foreign Application Priority Data

Feb. 2, 1977 [JP] Japan .................................. 52-9808

[51] Int. Cl.² ............................................... A61K 7/04
[52] U.S. Cl. ........................................ 424/61; 424/184
[58] Field of Search ................................. 424/61, 184

[56] References Cited

U.S. PATENT DOCUMENTS

| 3,896,014 | 7/1975 | Rosenberg | 204/159.23 |
| 3,928,113 | 12/1975 | Rosenberg | 204/159.14 |
| 4,058,442 | 11/1977 | Lee, Jr. et al. | 424/61 |

FOREIGN PATENT DOCUMENTS

| 928728 | 7/1949 | Fed. Rep. of Germany | 424/61 |
| 2112148 | 10/1972 | Fed. Rep. of Germany | 424/61 |
| 1201005 | 7/1959 | France | 424/61 |
| 471162 | 3/1952 | Italy | 424/61 |
| 601336 | 7/1960 | Italy | 424/61 |
| 50-19941 | 3/1975 | Japan . | |

OTHER PUBLICATIONS

Journal of the Amer. Pharm. Assoc., vol. 53, No. 6, pp. 336.
Levin, Manufacturing Chemist, 4/1955, vol. 26, No. 4, pp. 157–160.

*Primary Examiner*—Dale R. Ore
*Attorney, Agent, or Firm*—Toren, McGeady and Stanger

[57] ABSTRACT

A nail enamel composition prepared by dissolving a solid resin and an organopolysiloxane, particularly a copolymer having a polysiloxane structure and a polyoxyalkylene structure, together in an organic solvent. The composition forms a film on the surface of the finger-nail and the film thus formed can easily be peeled off.

8 Claims, No Drawings

NAIL ENAMEL COMPOSITION AND MANUFACTURING METHOD THEREOF

BACKGROUND OF THE INVENTION

1. Field of the Invention

The present invention relates to a novel and improved enamel composition useful for manicuring the finger-nails and capable of forming a film on the surface of the finger-nails, which can easily be peeled off without the aid of a remover. The invention also relates to a method of manufacturing the nail enamel composition.

2. Description of the Prior Art

Nail enamel compositions known hitherto are prepared from polymeric materials as the basic component or the film forming component, such as synthetic resins, e.g. an alkyd resin, polyvinyl acetate and a polyester, and cellulose derivatives, e.g. nitrocellulose and cellulose acetate. When one tries to remove the film of the conventional nail enamels from the surface of the finger-nail, the aid of remover in the form of solution, which usually contains an organic solvent, such as ketones, esters and the like, and can easily dissolve the film, is needed. This is why the remover is sold in the market side by side with nail enamel compositions.

The use of the remover to strip the coating films of the nail enamel off the surfaces of the finger-nails tends to simultaneously remove moisture and lipid components from the nail surfaces and consequently depriving the nail surfaces proper of luster and smoothness and further rendering the nails brittle, often resulting in making it impossible to keep the points of the nails in a neatly peaked form.

Further, the conventional nail enamel compositions contain an organopolysiloxane, such as dimethylpolysiloxane or methylphenylpolysiloxane, which serves to give higher gloss to the surface of the enamel-coated finger nail. The silicone compounds have any of the following molecular formulas end-blocked with trimethyl silyl groups.

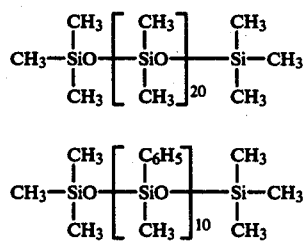

Those silicone compounds, however, adversely affect the peelability of the coating films from the nails, and have a poor compatibility with the solid resin component in the composition, so that the finished nail enamels are far from satisfaction.

The nail enamel composition, known as a coating composition for the finger-nails, is a kind of cosmetics with the purpose of treating or beautifying the finger-nails. However, it is undesirable to keep the nails coated with the nail enamel over a lengthy period of time because of harmful effects, such as the suppressed circulation of blood in the underlying tissues. Therefore, it is desired for one to strip the coating films off the nail surfaces at appropriate intervals, for example, once a day before going to bed. Nevertheless, the conventional nail enamel compositions are still harmful because of the necessitated use of the organic solvent-containing remover solution.

SUMMARY OF THE INVENTION

It is therefore the object of the present invention to provide an improved nail enamel composition free of the above-described defects and disadvantages encountered in the conventional like compositions.

In accordance with the present invention, the nail enamel composition comprises (a) 100 parts by weight of a natural or synthetic resin which is solid at room temperature and soluble in an organic solvent, and (b) from 0.01 to 30 parts by weight of a organopolysiloxane represented by the general formula $$R_a^1 R_b^2 SiO_{(4-a-b/2)}$$

where $R^1$ is a monovalent hydrocarbon group, $R^2$ is a group bonded directly to the silicon atom forming an Si—O— linkage or bonded to the silicon atom through an alkylene group selected from the class consisting of a hydroxy group; an alkoxy group; an ester residue represented by the general formula —OCOR$^3$ where $R^3$ is a monovalent hydrocarbon group; a polyoxyalkylene group represented by the general formula $$-(OC_2H_4)_q(OC_3H_6)_r-OA$$

where q and r are each zero or a positive integer but not equal to zero simultaneously and A is a hydrogen atom, an alkyl group or an acyl group; a thiol group; a group represented by the general formula —S—CH$_{2 t}$COOH where t is a positive integer; a glycidoxy group; an amino group; and an N-(aminoalkyl)-substituted amino group; and a and b are each positive numbers with the proviso that (a+b) is in the range from 1.8 to 3.0 inclusive, ingredients (a) and (b) being dissolved together in an organic solvent.

DETAILED DESCRIPTION OF THE PREFERRED EMBODIMENTS

The nail enamel composition of the present invention has a unique characteristic and may be classified as a new type of nail enamels. The composition has an immutable adhesiveness to the nail enamel when applied and thoroughly fulfills the intrinsic purpose of making-up the nails. The film once formed on the nails does not peel off wholly or even partially during usual kitchen work or by usual physical force from outside, for example, friction with cloth, but can be easily peeled from the nail surfaces in an unsupported and continuous form without leaving any segments torn behind, when intentionally pulled up by one edge, using no remover.

The nail enamel composition of the present invention comprises (a) 100 parts by weight of a natural or synthetic resin which is solid at room temperature and soluble in an organic solvent, and (b) from 0.01 to 30 parts by weight of an organopolysiloxane represented by the average unit formula $$R_a^1 R_b^2 SiO_{(4-a-b/2)} \tag{1}$$

where $R^1$ is a monovalent hydrocarbon group; $R^2$ is a group bonded directly to the silicon atom forming an Si-O-linkage selected from the class consisting of a hydroxy group; an alkoxy group; an ester residue represented by the general formula —OCOR$^3$ where $R^3$ is a monovalent hydrocarbon group; and a polyoxyalkylene group represented by the general formula

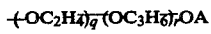

where q and r are each zero or a positive integer but not equal to zero simultaneously and A is a hydrogen atom, an alkyl group or an acyl group; or a group bonded to the silicon atom through an alkylene group selected from the class consisting of a hydroxy group; an alkoxy group; an ester residue represented by the general formula —OCOR$^3$; a polyoxyalkylene group represented by the general formula

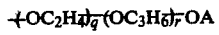

where q, r and A each have the same meaning as above; a thiol group; a group represented by the general formula

where t is a positive integer; a glycidoxy group; an amino group and an N-(aminoalkyl) substituted amino group; and a and b are each positive numbers with the proviso that (a+b) is in the range from 1.8 to 3.0 inclusive.

Further, according to the present invention, the nail enamel composition is prepared by dissolving ingredients (a) and (b) in an organic solvent.

The resin ingredient (a) useful in the composition of the present invention should be glossy, transparent, resilient, soft, water-repellent, rejectable to injury, and should further be well soluble in an organic solvent having a higher volatility at room temperature, such as a ketone or an ester. Example of the resins are copolymers of vinyl chloride and vinyl acetate, copolymers of an acrylic ester and vinyl acetate, copolymers of ethylene and viny acetate, polyvinyl acetate, alkyd resins, polyesters, sulfonamide resins, acetal resins, polyacrylic esters, polymethylacrylic ester resins, nitrocellulose, polyethyleneglycol, shellac, dammar and elemis. Most preferred among them are copolymers of vinyl chloride and vinyl acetate, sulfonamide resins, acetal resins, polyacrylic esters, polymethacrylic esters, and nitrocellulose. They are used either alone or in combination with any of the others. A resin having a comparatively low molecular weight and liquid at room temperature which is included in the conventional nail enamel composition so as to improve its adhesiveness to the nail, its grave appearance, its luster and its water-resistance, may be used for the formulation of the nail enamel composition of the invention. However, its amounts should not be too large, since large amounts used tend to result in producing a coating film which is torn when peeled and not smoothly peeled off in a continuous form. A suitable amount is at most 2% by weight of the whole formulation. Such low-molecular resins that are used for improving the appearance and luster of the coating film are, for example, a sulfonamide resin having an average molecular weight of from 1,000 to 2,000 and alkyd resin having an average molecular weight of from 1,000 to 2,000.

The organopolysiloxane ingredient (b) useful in the nail enamel composition of the invention that is represented by formula (1) has an effect of rendering the coating film of the nail enamel easily peelable off the nail surface when so intended.

The symbol R$^1$ in formula (1), represents non-substituted monovalent hydrocarbon groups exemplified by alkyl groups, such as methyl group, ethyl group, propyl group, butyl group and the like; alkenyl groups, such as vinyl group, allyl group and the like; aryl groups, such as phenyl group, tolyl group, xylyl group and the like; and aralkyl groups, such as benzyl group, phenyl ethyl group, 2-phenyl propyl group and the like.

The symbol R$^2$ in formula (1) represents a group bonded to the silicon atom forming an Si-O- linkage selected from the class consisting of a hydroxy group, an alkoxy group having carbon atoms not exceeding 20, such as methoxy group, ethoxy group, propoxy group, butoxy group, octoxy group and the like; an ester residue represented by the general formula -OCOR$^3$ where R$^3$ is a monovalent hydrocarbon group having from 1 to 20 carbon atoms and a polyoxyalkylene group represented by the general formula

where q and r are each zero or a positive integer but not equal to zero simultaneously and A is a hydrogen atom; an alkyl group or acyl group; or a group bonded to the silicon atom through an alkylene group selected from the class consisting of a hydroxy group; an alkoxy group; an ester residue represented by the general formula —OCOR$^3$; a polyoxyalkylene group represented by the general formula

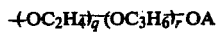

where q, r and A each have the same meaning as above; a thiol group, a group represented by the general formula

where t is a positive integer; a glycidoxy group; an amino group and an N-(aminoalkyl) substituted amino group; and a and b are each positive numbers with the proviso that (a+b) is in the range from 1.8 to 3.0 inclusive.

Among the organopolysiloxanes represented by formula (1), those having the copolymeric molecular structure of siloxane units and oxyalkylene units are most preferred. They are represented by any of the following three general formulas.

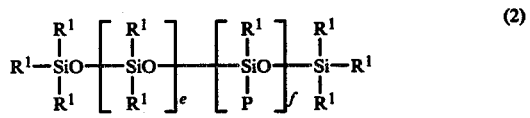

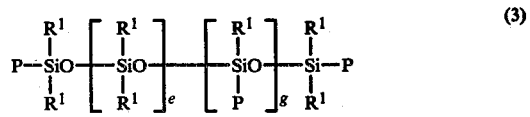

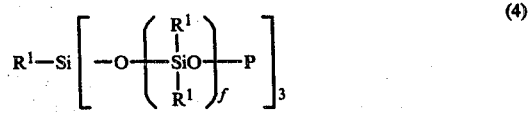

In the above formulas, P is a polyoxyalkylene group represented by the general formula

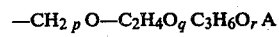

where p is zero or a positive integer of from 1 to 20, q and r are each zero or a positive integer not exceeding 100 but not equal to zero simultaneously, and (q+r) is from 1to 100; e is zero or a positive integer of from 1 to 1000, f is a positive integer of from 1 to 100, and g is zero or a positive integer of from 1 to 100.

The coating film of the nail enamel composition containing the above-specified organopolysiloxane and formed on the finger-nail does not peel spontaneously off the surface of the nail by usual physical influences, such as friction with a cloth or during the usual kitchen work, but can easily and uniformly be peeled off by intentionally lifting and pulling the edge of the film. In this peeling operation no remover is required. Therefore, a noteworthy advantage is obtained in the removal of the film once formed of the composition according to the present invention that the procedure of roughening the coated surface of the nail which is possibly accompanied by the removal of lipids, the loss of gloss and, what is worse, the brittleness of the nail can be omitted. Another advantage of the composition of the invention is that an increased gloss of the coating film is obtained.

The compounding ratios of ingredients (a) and (b) in the composition of the invention should be set forth in order to attain the above advantages most effectively. Ingredient (b) should be compounded in an amount of not less than 0.01 part by weight or, in particular, not less than 0.5 part by weight, per 100 parts by weight of ingredient (a), while the same ingredient (b) should be included in an amount exceeding 30 parts by weight or, in particular, 15 parts by weight on the a similar basis, since any larger amounts no longer work to improve the composition, but deteriorate the physical properties of the resulting coating film, such as mechanical strengths, that are required for the desired nail enamel compositions. Besides, the use of large amounts naturally results in higher production costs, and the use of ingredient (b) in an amount of more than the above maximum should be avoided from such economical point of view also.

The nail enamel composition of the present invention is prepared by dissolving the above-described solid resin and organopolysiloxane in an organic solvent optionally with the addition of a coloring matter, plasticizer, perfumery, and lustering material, e.g. titanated mica and/or bismuth oxychloride.

Illustrative of the organic solvent useful for the purpose are alcohols, such as ethyl alcohol, isopropyl alcohol, n-butyl alcohol, amyl alcohol and the like; ketones, such as acetone, methylethyl ketone and the like; esters, such as ethyl acetate, butyl acetate and the like; glycol ethers, such as ethyleneglycol monobutyl ether, diethyleneglycol monoethyl ether and the like; and hydrocarbons, such as toluene, n-hexane and the like. A single solvent or mixture of solvents can be used.

The sequence of dissolving the solid resin, the organopolysiloxane and the other optional components in the organic solvent is not critical. All the ingredients may be simultaneously or successively dissolved in a single solvent or a mixture of solvents. Or, for example, the organopolysiloxane is dissolved in one of the organic solvents, and the solution is mixed with another organic solution of the other ingredient or ingredients. However, since no homogeneous solution can always be obtained when the organopolysiloxane is added to the organic solution of the solid resin, it is preferred to add the solid resin or the organic solution of the solid resin into the organic solution of the organopolysiloxane.

Suitable concentrations of the solid resin in the solution are in a range from about 10 to 30% by weight, while the organopolysiloxane may be present in the varied amounts within the range as set forth above based on the solid resin.

In order to further improve the compatibility or homogeneity among the solutes, i.e. the solid resin, the organopolysiloxane and the other optional ingredients, or particularly between the solid resin and the organopolysiloxane, the organic solution is heated at a temperature from 40° C. to the boiling point of the organic solvent during or after the preparation of the solution. The compatibility among the ingredients or, in particular, between the solid resin and the organopolysiloxane, is increased by the heating treatment and the homogeneity of the solution is improved, thus giving the easiness of peeling which is the intrinsic object of the present invention.

The nail enamel composition of the present invention is highly homogeneous and stable, and the nail enamel films formed exhibit graceful luster and are hardly removed off by friction, minute impulse or contact with water during the kitchen work, thus keeping the coated nail surfaces unharmed and, on the other hand, the coating films can be peeled off as a continuum and without leaving any fragments only by lifting and pulling the edge of the film when so desired.

The nail enamel composition of the invention per se may of course be applied direct to the nail surfaces. As an alternative, the nail enamel composition of the invention is applied on the nail surfaces as the undercoat, overlying which a conventional nail enamel composition is applied. The thus formed two-layer coating film can also be peeled off in a satisfactory manner and without the aid of the remover.

The present invention will further be illustrated by the following examples.

EXAMPLE 1

(Experiments 1 to 18)

Colorless nail enamel compositions were prepared by compounding together an single resin or a combination of resins, an organopolysiloxane and dibutyl phthalate in the varied amounts (parts by weight) as indicated in the table in a mixture of solvents consisting of 5 parts by weight of ethyl alcohol, 5 parts by weight of ethyl acetate, 30 parts by weight of butyl acetate and 30 parts by weight of toluene.

Each of the nail enamel composition thus prepared was applied to the surface of the finger nail in a usual manner, and allowed to stand for 6 hours. Then, the coating films formed on the nail surfaces were tested for peeling by lifting and pulling the edge of the film. The peeling test results are set out in the table.

In the table:

R-1: Polyvinyl butyral resin with an average molecular weight of about 200,000.
R-2: A copolymer of 87% by mole of vinyl chloride and 13% by mole of vinyl acetate with an average molecular weight of about 150,000.
R-3: Nitrocellulose.
R-4: A liquid resin obtained by mixing equal amounts of polybutyl acrylate with an average molecular weight of about 2,000 and polybutyl methacrylate with an average molecular weight of about 2,000.

-continued

R-5: A sulfonamide resin with an average molecular weight of about 1,000 (a liquid resin).
R-6: Polybutyl acrylate with an average molecular weight of about 10,000.
R-7: A sulfonamide resin with an average molecular weight of about 10,000.
R-8: Polymethyl methacrylate resin with an average molecular weight of about 100,000.

S-1:
$$Me-SiO\underset{Me}{\overset{Me}{|}}\left[SiO\underset{Me}{\overset{Me}{|}}\right]_{80}\left[SiO\underset{P^1}{\overset{Me}{|}}\right]_{8}Si-Me\underset{Me}{\overset{Me}{|}}$$
$P^1 = -CH_2CH_2CH_2O-(C_2H_4O)_{10}H$
Me = Methyl group S-2:
$$Me-SiO\underset{Me}{\overset{Me}{|}}\left[SiO\underset{P^2}{\overset{Me}{|}}\right]_{38}Si-Me\underset{Me}{\overset{Me}{|}}$$
$P^2 = -CH_2CH_2CH_2O-(C_2H_4O)_{3}H$
Me = Methyl group S-3:
$$Me-SiO\underset{Me}{\overset{Me}{|}}\left[SiO\underset{P^3}{\overset{Me}{|}}\right]_{5}\left[SiO\underset{Me}{\overset{Me}{|}}\right]_{25}Si-Me\underset{Me}{\overset{Me}{|}}$$
$P^3 = -CH_2CH_2CH_2O-(C_2H_4O)_{10}-(C_3H_6O)_{10}\overset{O}{\overset{||}{C}}Me$
Me = Methyl group S-4:
$$Me-Si\left[-O-\left(SiO\underset{Me}{\overset{Me}{|}}\right)_{10}-P^4\right]_{3}$$
$P^4 = -(C_2H_4O)_{30}-(C_3H_6O)_{10}C_4H_9$
Me = Methyl group S-5:
$$Me-SiO\underset{Me}{\overset{Me}{|}}\left[SiO\underset{P^5}{\overset{Me}{|}}\right]_{2}\left[SiO\underset{Me}{\overset{Me}{|}}\right]_{10}Si-Me\underset{Me}{\overset{Me}{|}}$$
$P^5 = -O-(C_3H_6O)_{18}Me$
Me = Methyl group S-6:
$$C_2H_5O\left[SiO\underset{Me}{\overset{Me}{|}}\right]_{40}\left[SiO\underset{CH_2CH_2CH_2SH}{\overset{Me}{|}}\right]_{4}C_2H_5$$
Me = Methyl group S-7:
$$Me-SiO\underset{Me}{\overset{Me}{|}}\left[SiO\underset{Me}{\overset{Me}{|}}\right]_{25}\left[SiO\underset{Q^1}{\overset{Me}{|}}\right]_{10}Si-Me\underset{Me}{\overset{Me}{|}}$$
$Q^1 = -CH_2CH_2-S-CH_2CH_2CH_2COOH$
Me = Methyl group S-8:
$$Me-SiO\underset{Me}{\overset{Me}{|}}\left[SiO\underset{Me}{\overset{Me}{|}}\right]_{800}\left[SiO\underset{Q^2}{\overset{Me}{|}}\right]_{30}Si-Me\underset{Me}{\overset{Me}{|}}$$
$Q^2 = -CH_2CH_2CH_2O-CH_2CH\underset{\diagdown O \diagup}{-}CH_2$
Me = Methyl group S-9:
$$Me-SiO\underset{Me}{\overset{Me}{|}}\left[SiO\underset{C_{12}H_{25}}{\overset{Me}{|}}\right]_{2}\left[SiO\underset{OCOC_{17}H_{35}}{\overset{Me}{|}}\right]_{2}Si-Me\underset{Me}{\overset{Me}{|}}$$
Me = Methyl group S-10:
$$Q^3-Si\left[\left(OSi\underset{Me}{\overset{Me}{|}}\right)_{10}OC_2H_5\right]_{3}$$
$Q^3 = -CH_2CH_2CH_2NHCH_2CH_2NH_2$
Me = Methyl group S-11:
$$Me-SiO\underset{Me}{\overset{Me}{|}}\left[SiO\underset{Me}{\overset{Me}{|}}\right]\left[SiO\underset{CH_2CH_2CH_2OH}{\overset{Me}{|}}\right]_{20}\left[SiO\underset{Me}{\overset{Me}{|}}\right]_{20}Si-Me\underset{Me}{\overset{Me}{|}}$$
Me = Methyl group S-12:
$$HO\left[SiO\underset{Me}{\overset{Me}{|}}\right]_{10}H$$
Me = Methyl group Rating of Peelability A: The film could be uniformly peeled off with easiness.
B: The film could be peeled off in the form of a continuum, but with resistance to separation.
C: The film was peeled off but torn in pieces.
D: The film was found strongly adhering to the nail surface, and peeling was almost impossible.

TABLE

| Exp. No. | Resin | Parts | Organopoly-siloxane | Parts | Dibutyl phthalate (parts) | Rating of peelability |
|---|---|---|---|---|---|---|
| 1 | R-1 | 20 | S-1 | 3 | 3 | A |
| 2 | R-1 | 20 | S-1 | 0.5 | 3 | B |
| 3 | R-1 | 20 | S-1 | 0.1 | 3 | B |
| 4 | R-1 | 20 | S-2 | 1 | 3 | A |
| 5 | R-1 | 20 | S-3 | 1 | 3 | A |
| 6 | R-2 | 20 | S-4 | 1 | 3 | A |
| 7 | R-2 | 20 | S-5 | 1 | 3 | A |
| 8 | R-1 | 3 | S-6 | 1 | 4 | B |
|  | R-3 | 12 |  |  |  |  |
|  | R-1 | 15 |  |  |  |  |
| 9 | R-5 | 1 | S-7 | 1 | 3 | B |
|  | R-7 | 4 |  |  |  |  |
|  | R-3 | 10 |  |  |  |  |
| 10 | R-7 | 5 | S-8 | 1 | 4 | B |
|  | R-3 | 10 |  |  |  |  |
| 11 | R-4 | 1 | S-9 | 1 | 4 | B |
|  | R-6 | 5 |  |  |  |  |
|  | R-12 | 15 |  |  |  |  |
| 12 | R-6 | 5 | S-10 | 1 | 3 | B |
| 13 | R-1 | 20 | S-11 | 1 | 3 | B |
| 14 | R-1 | 20 | S-12 | 1 | 3 | B |
|  | R-3 | 10 |  |  |  |  |
| 15* |  |  | none |  | 4 | D |
|  | R-5 | 10 |  |  |  |  |
|  | R-3 | 10 |  |  |  |  |
| 16* |  |  | none |  | 4 | D |
|  | R-4 | 10 |  |  |  |  |
|  | R-3 | 10 |  |  |  |  |
| 17* |  |  | S-1 | 1 | 4 | C |
|  | R-5 | 10 |  |  |  |  |
| 18 | R-8 | 20 | S-1 | 1 | 6 | A |

*Comparative experiments.

EXAMPLE 2

(Experiment 19)

The nail enamel composition prepared in Experiment 2 of Example 1 was subjected to heating at 60° C. for 2 hours. The nail enamel composition thus heated was then applied to the finger nail surface, and allowed to stand for 6 hours. Then the coating film formed on the nail surface was tested for peeling in the same manner as in Example 1. As a result, rating A of peelability was determined.

EXAMPLE 3

(Experiments 19 and 20)

For the purpose of comparison, the same procedure for preparing the composition of Experiment 1 of Example 1 was repeated except that, instead of 3 parts of organopolysiloxane S-1, one part of a dimethylpolysiloxane represented by the formula

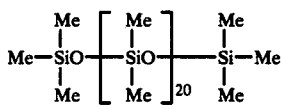

(in Experiment 20) or one part of a dimethylpolysiloxane represented by the formula

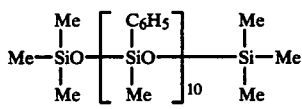

(in Experiment 21) was used.

The resulting liquid compositions were observed to be in an inhomogeneous state. Each composition thus prepared was applied to the nail surface, and allowed to stand for 6 hours. Thereupon, the coating films formed on the nail surface were subjected to a similar peeling test to determine the rating of peelability. As a result, rating C and D were obtained in Experiments 20 and 21, respectively.

What is claimed is:

1. A nail enamel composition comprising
   (a) 100 parts by weight of a natural or synthetic resin which is solid at room temperature and soluble in an organic solvent, and
   (b) from 0.01 to 30 parts by weight of an organopolysiloxane of the formula

where $R^1$ is a monovalent hydrocarbon, $R^2$ is bonded directly to the silicon atom forming a Si-O-linkage selected from the group consisting of hydroxy, alkoxy; a residue of the formula —OCOR$^3$ where $R^3$ is a monovalent hydrocarbon, and a polyoxyalkylene of the formula

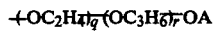

where q and r are each zero or a positive integer but not equal to zero simultaneously and A is hydrogen, alkyl or an acyl, or a group bonded to the silicon atom through an alkylene selected from the group consisting of hydroxy, alkoxy and a residue of the formula —OCOR$^3$, a polyoxyalkylene of the formula

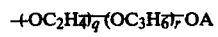

where q, r and A each have the same meaning as above; a thiol group; a group of the formula

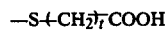

where t is a positive integer, a glycidoxy, an amino, and an N-(aminoalkyl) substituted amino; and a and b are each positive numbers with the proviso that (a+b) is in the range from 1.8 to 3.0 inclusive and an organic solvent.

2. The nail enamel composition as claimed in claim 1 wherein said natural or synthetic resin is selected from the group consisting of a copolymer of vinyl chloride and vinyl acetate, a sulfonamide resin, an acetal resin, a polyacrylic ester, a polymethylacrylic ester and nitrocellulose.

3. The nail enamel composition as claimed in claim 1 wherein said organopolysiloxane is a copolymer containing the polysiloxane structure and the polyoxyalkylene structure.

4. The nail enamel composition as claimed in claim 1 wherein from 0.5 to 30 parts by weight of said organopolysiloxane is compounded per 100 parts by weight of said natural or synthetic resin.

5. A method of manufacturing a nail enamel composition comprising dissolving in an organic solvent
   (a) 100 parts by weight of a natural or synthetic resin which is solid at room temperature and soluble in an organic solvent, and
   (b) from 0.01 to 30 parts by weight of an organopolysiloxane of the formula

where $R^1$ is a monovalent hydrocarbon, $R^2$ is bonded directly to the silicon atom forming a Si-O-linkage selected from the group consisting of hydroxy, alkoxy, a residue of the formula —OCOR$^3$ where $R^3$ is a monovalent hydrocarbon, and a polyoxyalkylene of the formula

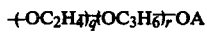

where q and r are each zero or a positive integer but not equal to zero simultaneously and A is hydrogen, alkyl or an acyl, or a group bonded to the silicon atom through an alkylene selected from the group consisting of hydroxy, alkoxy, and a residue of the formula —OCOR$^3$, a polyoxyalkylene of the formula

where q, r and A each have the same meaning as above, a thiol group, a group of the formula

where t is a positive integer, a glycidoxy, an amino, and an N-(aminoalkyl) substituted amino; and a and b are each positive numbers with the proviso that (a+b) is in the range from 1.8 to 3.0 inclusive.

6. The method of manufacturing a nail enamel composition as claimed in claim 5 wherein said organic solvent is selected from the group consisting of isopropyl alcohol, ethyl acetate, butyl acetate and toluene.

7. The method of manufacturing a nail enamel composition as claimed in claim 5 wherein said natural or synthetic resin is dissolved in said organic solvent in an amount sufficient to obtain a concentration of from 10 to 30% by weight in the solution.

8. The method of manufacturing a nail enamel composition as claimed in claim 5 wherein ingredients (a) and (b) are heated together at a temperature from 40° C. to the boiling temperature of said organic solvent.

* * * * *